United States Patent [19]

Björck et al.

[11] Patent Number: 5,108,894
[45] Date of Patent: Apr. 28, 1992

[54] PROTEIN G AND/OR FRAGMENTS THEREOF

[75] Inventors: Lars Björck, Södra Sandby; Göran Kronvall; Gunnar Lindahl, both of Lund, all of Sweden; William H. Kastern, Søborg, Denmark

[73] Assignee: Pharmacia LKB Biotechnology AB, Sweden

[21] Appl. No.: 376,160

[22] Filed: Jul. 5, 1989

Related U.S. Application Data

[63] Continuation of Ser. No. 857,764, Apr. 30, 1986, abandoned.

[30] Foreign Application Priority Data

May 3, 1985 [SE] Sweden .............................. 8502162

[51] Int. Cl.$^5$ .......................... C12Q 1/68; C12Q 1/00; C12P 21/02; C12P 19/34; C12N 15/00; C12N 7/00; C12N 1/21; C12N 15/70; C12N 15/72; C07H 15/12; C07K 3/00

[52] U.S. Cl. ..................................... 435/6; 435/7.32; 435/7.34; 435/69.1; 435/91; 435/172.3; 435/252.3; 435/252.33; 435/235.1; 435/320.1; 536/27; 530/350; 935/19; 935/29; 935/31; 935/41; 935/56; 935/58; 935/61; 935/73

[58] Field of Search .................. 435/68, 172.1, 172.3, 435/252.33, 320.1, 69.1, 235.1, 91, 7.1, 7.2, 235.1; 536/27; 530/350; 935/19, 31, 41, 58, 60, 73, 81

[56] References Cited

U.S. PATENT DOCUMENTS

| | | | |
|---|---|---|---|
| 4,617,266 | 10/1986 | Fahnestock | 435/6 |
| 4,900,660 | 2/1990 | Boyle et al. | 435/7 |
| 4,945,157 | 7/1990 | Boyle et al. | 530/409 |
| 4,948,874 | 8/1990 | Kronvall et al. | 530/350 |
| 4,954,618 | 9/1990 | Fahnestock | 530/387 |
| 4,956,296 | 9/1990 | Fahnestock | 435/252.33 |
| 4,977,247 | 12/1990 | Fahnestock et al. | 530/387 |

FOREIGN PATENT DOCUMENTS

0107509 5/1984 European Pat. Off. .
0124374 11/1984 European Pat. Off. .
0131142 1/1985 European Pat. Off. .

OTHER PUBLICATIONS

Holt, R. G. et al, *Infec. and Immun.*, vol. 38, pp. 147–156 (1982).
Shea, C. et al., *Infec. and Immun.*, vol. 34, pp. 851–855 (1981).
Kronvall, G., *J. Immunol.*, vol. 111, pp. 1401–1405 (1973).
Reis, K. J., et al., *J. Immunol.* 132:3098–3102 (1984).
Bjorck and Kronvall, *J. Immunol.* 133:969–974 (1984).
Reis, K. J., et al., *J. Immunol.* 132:3091–3097 (1984).
Boyle, M. D. P., *Biotechniques* 334–340 (1984).
Myhre, E. B. et al., *Infect. Immun.* 17:475–482 (1977).
Myhre, E. B. et al., *Infect. Immun.* 23:1–7 (1979).
Schalen, C. et al., *Acta Path. Microbiol. Immunol. Scand Sect. B* 91:27–33 (1983).
Christensen, P. et al., *Acta Path. Microbiol. Scand. Sect. C* 84:196–202 (1976).
Claverys et al., *Gene* 13:65–73 (1981).
Russell et al., *FEMS Microbiol. Lett.* 30:37–41 (1985).
Gilpin et al., *Infect. Immun.* 49:414–416 (1985).
Malke and Ferretti, *Proc. Natl. Acad. Sci. USA* 81:3557–3561 (1984).
Russell et al., *J. Gen. Microbiol.* 131:295–299 (1985).
Lafdahl, S. et al., *Proc. Natl. Acad. Sci. USA* 80:697–701 (1982).

*Primary Examiner*—Joan Ellis
*Attorney, Agent, or Firm*—Sterne, Kessler, Goldstein & Fox

[57] ABSTRACT

A hybrid DNA molecule is disclosed by this invention capable of cellular expression comprising the DNA sequence for protein G. Said DNA sequence has substantially the same IgC binding properties as naturally occurring protein G. The molecule may be comprised of DNA sequences coding for fragments of protein G. Moreover, said DNA sequence may code for both fragments of protein G and protein G. The DNA sequence can be isolated from streptococcal DNA.

17 Claims, No Drawings

PROTEIN G AND/OR FRAGMENTS THEREOF

This is a continuation of application Ser. No. 06/857,764 filed Apr. 30, 1986 now abandoned.

FIELD OF THE INVENTION

The present invention relates to hybrid DNA technology. More particularly, the present invention relates to a technique for the preparation of protein G and/or fragments thereof with the capability of binding immunoglobulin G (IgG).

For more detailed information regarding protein G reference is made to J. Immunol. 133:969, 1984 together with Swedish patent application no. 8303578-2, which was filed on Jun. 2, 1983, and which corresponds to U.S. Pat. application Ser. No. 619,820, filed on Jun. 12, 1984.

BACKGROUND OF THE INVENTION

Up to now the method used for the preparation of protein G is that described in the above-mentioned publications. It is based on liberating the protein from the surface of streptococcal bacteria with the help of proteolytic enzymes, whereafter the protein is isolated.

This method has serious disadvantages. For example, only a part of the protein G molecule is liberated from the bacterial surface, and even if this part is clearly capable of binding IgG, it would still be advantageous to isolate the whole molecule. Moreover, this method is restricted to the use of streptococci as a starting material, and bearing in mind that these are pathogens and difficult to cultivate on a large scale, it would be desirable to find a method which can apply to other starting materials.

Thanks to the advent of modern genetic engineering, and specifically hybrid DNA technology, improved techniques have become available for the preparation of proteins with particularly attractive properties. The technique begins by locating the genetic information which codes for the desired protein. This genetic information is transferred using vectors from one cell to another. As a result of this transformation, the transformed cell, hitherto unable to synthesize the desired protein, may become capable of producing the desired protein. Such a method has been used for the synthesis of protein A (a cell wall protein of S. aureus) and is described in two Swedish patent applications, Nos. 8204810-9 and 8204811-7, and two European patent applications, Nos. 0 107 509 and 0 124 374.

Compared with protein A, protein G has substantial advantages, especially as a therapeutic agent for removal of antigen-antibody complexes from the blood during extracorporeal blood treatment in connection with certain autoimmune sicknesses. For example, protein G binds to all IgG subclasses, whereas protein A lacks the ability to bind human IgG 3. Furthermore, protein G is a more selective Fc receptor than protein A, since it does not bind immunoglobulin A and immunoglobulin M.

It is therefore an object of the present invention to provide, using hybrid DNA technology, a method for the preparation of protein G and/or fragments of protein G with substantially the same properties as protein G insofar as the capability of binding IgG is concerned. This and other objects have been achieved in accordance with the invention, described in detail below.

SUMMARY OF THE INVENTION

In accordance with the present invention, these and other objects have now been attained by the presence of a hybrid DNA molecule which is capable of cellular expression comprising the DNA sequence for protein G. said sequence codes for a protein with substantially the same IgG binding properties as naturally occurring protein G. In a preferred embodiment, the molecule may be comprised of DNA sequences coding for fragments of protein G. Moreover, the DNA sequence may code for both fragments of protein G and protein G. The DNA sequence can be isolated from streptococcal DNA.

In accordance with another embodiment of the present invention, a cell transformed by a hybrid DNA molecule encoding the protein G binding site for IgG is provided. The cell may also encode fragments of protein G as well as protein G itself. The type of cell used may vary but can include Gram negative bacteria, Gram positive bacteria, yeast cells and plant cells. Specifically, bacteria of the species E. coli can be used. The encoding DNA molecule may be derived from streptococcal DNA.

In accordance with the method of the present invention, the IgG binding site of protein G is prepared. The method comprises extracting DNA fragments coding for the IgG binding site of protein G by disrupting bacterial cell walls. The extracted DNA is cleaved using restriction enzymes, into fragments of a size enabling introduction of the DNA into designated vector. A cell, not normally capable of producing the IgG binding site of protein G, is transformed with the use of this vector. The cell is cultivated and, subsequently, the IgG binding site of the protein G synthesized by the cell is isolated. As a result, the cell is transformed into a cell which produces the IgG binding site for protein G wherein the binding site has substantially the same binding properties as naturally occurring protein G IgG binding sites. The DNA fragments extracted for use in this transformation may be derived from streptococcal DNA. A variety of cells may be used in the transformation including Gram negative bacteria, Gram positive bacteria, yeast cells and plant cells. Specifically, bacteria of the species E. coli can be used. The DNA fragments may encode the entire protein G or fragments thereof. The IgG binding sites of protein G may be enzymatically or radioactively marked and said binding sites are capable of binding peroxidase marked IgG.

DETAILED DESCRIPTION

A hybrid DNA molecule is produced comprising a vector into which has been introduced a DNA sequence coding for a protein capable of being expressed in a cell. The hybrid DNA molecule is characterized in that the DNA sequence codes for protein G and/or fragments of protein G with substantially the same properties as naturally occurring protein G insofar as the ability to bind IgG is concerned.

A cell is also produced which has been transformed by a vector comprising a hybrid DNA molecule into which has been introduced a DNA sequence encoding a polypeptide capable of expression in the cell. Specifically, the polypeptide encoded by the DNA sequence is protein G and/or fragments of protein G which comprise the binding site for IgG. The properties of the IgG binding site are substantially the same, insofar as the capacity of IgG binding is concerned, as is found in naturally occurring protein G.

Moreover, a method is provided for the preparation of protein G and/or fragments of protein G with substantially the same properties as protein G, again insofar as the capability of binding IgG is concerned. The method involves the incorporation into a host cell, in the currently preferred embodiment of a microbial cell, of a hybrid DNA molecule using a vector into which has been introduced a DNA sequence encoding a protein capable of being expressed in the cell, and which is characterized in that the DNA sequence codes for protein G and/or fragments of protein G with substantially the same properties as protein G, insofar as the capability of binding IgG is concerned.

In accordance with the invention, a DNA fragment is isolated from streptococcal bacteria. By way of example, DNA from group A, C or G streptococci may be used, but preferably group C and/or group G streptococcal DNA is used. Conventional techniques are used including application of restriction enzymes which cleave the isolated DNA into suitably sized DNA fragments. The size of the DNA fragments may vary and depend, among other things, on the type of vector selected to accomplish the transformation.

Examples of vectors which can be used for the cloning in this invention include bacterial plasmids (e.g. plasmids from E. coli), phage DNA (e.g. phage lambda or derivatives of lambda, such as EMBL 3 and gt 11), vectors obtained from combinations of plasmids and phage DNA, yeast plasmids, and the like. The selection of vectors is made in consideration of the host cell to be used for expression. Such selection can readily be made by those versed in the art. The method of introducing the proper DNA fragment into the vector is the conventional method and is accomplished using ligating enzymes.

Suitable host cells which can be transformed by the hybrid DNA molecule of this invention, and which consequently become capable of producing the said protein G and/or fragments thereof, comprise Gram negative bacteria, specifically E. coli in the currently prefered embodiment, Gram positive bacteria, yeast cells, plant cells, and the like.

The following examples are merely intended to illustrate a practical mode of procedure for realizing the invention and are not intended to limit the invention in any way.

1. Isolation of chromosomal streptococcal DNA

As a starting material a group G streptococcal strain (G148) was selected predicated on high protein G content.

A culture of G148 bacteria in Todd-Hewitt (T-H) medium was allowed to grow overnight at 37° C. 3.0 ml of the culture were added to 225 ml T-H and incubated for 3 hours at 37° C. 13.6 ml of 10% cysteine and 11.25 ml of 0.4% DL-threonine were added. After incubation for 1 hour at 37° C., 125 ml of 15% glycine were added. After a further incubation of 45 minutes at 37° C., the cells were washed 3 times in 0.2M NaOAc and resuspended in 10 ml of 01.M Tris-HCl buffer, pH 8.0, containing 25% glucose and 10 mM EDTA. 20 mg lysozyme dissolved in 2.0 ml TE buffer (0.01M Tris-HCl, pH 7.4, containing 1.0 mM EDTA) were added. Then incubation took place for one hour at 37° C., whereupon 1.1 ml of 10% SDS dissolved in TE buffer were added. 500 microliters of proteinase K (Merck, Darmstadt, West Germany) dissolved in 0.1M Tris-HCl, at a pH of 7.4, in a concentration of 20 mg/ml and autodigested for 2 hours at 37° C. was added. After incubation overnight at room temperature 40 ml of TE buffer and 5 ml of 3 M NaOAc, at a pH of 7.4 were added. Then 150 ml of absolute alcohol were added, whereupon the solution was incubated at −20° C. overnight. After centrifuging at 2000 ×G for 30 minutes the supernatant was decanted. The pellet was washed two times with 80% alcohol, evaporated under nitrogen gas and dissolved in 4 ml of TE buffer, 500 microliters of RNase-A from bovine pancreas (Sigma, Mo, USA), and 2 mg/ml in 0.15 M NaCl heated to 80° C. were added prior to use. After incubation for 2 hours at 37° C., 200 microliters of proteinase K were added. After further incubation overnight at room temperature, the solution was twice phenol extracted at room temperature and dialyzed 3 times against TE buffer. 3 M NaOAc was added to a concentration of 0.3 M, whereupon 3 volumes of absolute alcohol were added. After incubation at −20° C. overnight centrifugation was carried out at 2000 ×G for 30 minutes. The pellet was washed twice with 80% alcohol and evaporated under nitrogen gas. Subsequently, the pellet was dissolved in 25 ml of TE buffer. 25 g of cesium chloride (BRL, Bethesda, USA) and 1 ml of ethidium bromide (5 mg/ml) (Sigma, Mo, USA) were added. After centrifugation at 138,000 ×G for 20 hours the DNA band, visualized with ultraviolet light and ethidium bromide, was drawn off. Two extractions with absolute butanol were followed by dialysis of the bottom phase against the TE buffer, whereupon NAOAc was added to 0.3 M. This was followed by alcohol precipitation with absolute alcohol and washing twice with 80% alcohol. The pellet was dissolved in distilled water.

2. Cloning of streptococcal DNA in EMBL 3 lambda vector

A derivative of phage lambda was used as a vector for purified streptococcal DNA fragmented by restriction enzymes. The derivative, EMBL 3, is commercially available (Promega Biotec, WI, USA). The procedure as to how the phage DNA and the foreign DNA are prepared and cleaved by restriction enzymes, and how the DNA fragments are ligated, has been described in detail in J. Mol. Biol. 170:827, 1983. In accordance with this known procedure, streptococcal DNA fragments in a size range of 10-25 kb (determined by gel electrophoresis in 1% agarose) were incorporated in EMBL 3 DNA. Lambda streptococcal hybrid DNA molecules were enclosed in the protein shell which marks an intact phage lambda capable of infection. A description of how this takes place can be found in the Promega Biotecs catalogue entitled "Promega Biotec, Molecular Biologicals". The end result was phage lambda containing lambda DNA molecules into which fragments of varying sizes of streptococcal DNA had been incorporated.

3. Infection of E. coli bacteria by EMBL 3 lambda phage containing streptococcal DNA Two E. coli strains, NM 538 and NM 539, were selected as host cells for production of the lambda streptococcal hybrid DNA molecules. These strains can be infected by EMBL 3 phages and are described in detail in J. Mol. Biol. 170:827, 1983. The strains were obtained from Promega Biotec. A bacterial colony of each strain was inoculated overnight in 20 ml LB medium (10g NaCl, 10g Difco tryptone, 5g Difco yeast extract, pH adjusted to 7.4 with 5M NaOH) containing maltose. 100 microlitres of phage solution (according to 2 above) were blended with 200 microliters of NM 538 and NM 539 bacteria. Thereafter, they were incubated for 30 minutes at 37° C. To both tubes 3 ml of LB maltose medium containing 10 mg of $MgCl_2$ and 0.7% agarose was added. The solutions (60° C.) were poured out onto LB plates (made of LB medium containing 1.5% agar), and a thin agarose layer was formed when the agarose solidified. The plates were incubated overnight at 37° C.

If the bacteria are not infected, a uniform mat of cells would cover the plates. Contrastingly, in the event of infection clear zones or plaques are formed in the cell mat. Plaques are formed because phage infected *E. coli* bacteria are lysed by the phages. When lysis occurs the cells burst, and the phages and other intracellular material formerly inside the cell spill out.

In this case, 500–2000 plaques/plate appeared. On the assumption that the EMBL 3 phages contain streptococcal DNA coding for the IgG binding sites of protein G, and on the assumption that this DNA can be replicated and expressed in *E. coli*, production of the IgG protein G binding sites can take place in the infected bacteria. Detection of these protein G sites in corresponding plaques is possible when bacteria lyse owing to phage infection, and release their contents. Of course, it is necessary to bear in mind that the streptococcal DNA fragments which have been incorporated in EMBL 3 DNA molecules are approximately 20 kb in size, and that the streptococcal genome amounts to several thousand kb. Therefore, only a statistically small number of the plaques should contain protein G.

4. Identification of plaques containing protein G

For the detection of protein G in these plaques, the ability of the molecule to bind IgG was exploited. Nitrocellulose filters (BA 85 Membranfilter, Schleicher and Schuell, Dassel, West Germany) were placed on top of the plate containing plaques for 10 minutes at room temperature. Proteins, phages and other material from the plates were absorbed into the filters. In order to block the continued facility of the filters to bind proteins, the filters were placed into a special blocking buffer (31.1 ml 5M NaCl, 10.0 ml 1M Tris HCl, pH 7.4, 50 ml Tween 20, distilled water added to 1 liter and 0.25 g gelatin). The buffer was changed 4 times every tenth minute (100 ml buffer each time), whereupon the filters were placed in 100 ml of blocking buffer, containing 200 microliters of peroxidase marked rabbit IgG (DAKO-Immunoglobulins A/S, Denmark) and treated on a shaker for 30 minutes at room temperature. If protein G has been absorbed by the filters the peroxidase marked Ig antibodies will be bound to the filters. The filters were again washed 4 times with blocking buffer and were placed into a fresh coloring solution (4 ml of 1% 3-amino-9-ethylcarbazol +100 ml of 50 mM NaOAc, pH 5.1+10 microliters $H_2O_2$), whereupon the peroxidase marked IgG antibodies bound to the filters emerged as brightly shining red spots. On the filter under test, a total of 26 red, shining pinhead sized spots, out off a total of approximately 6000 plaques, were observed. As a positive check, a filter was used onto which had been applied 0.25 micrograms of pure protein G (isolated according to J. Immunol. 133:969, 1984) in one microliter of distilled water, whereupon the filter was treated in the same manner as the others. A brightly shining red spot appeared where the protein G had been applied, whilst the remainder of the filter was white.

From the original plates the plaques corresponding to the ten strongest coloured red spots on the filter were then picked up with a Pasteur pipette. This material was washed into ten tubes, each containing 1 ml SM buffer (20 mM Tris-Hcl, pH 8.0, 0.1M NaCl, 10 mM $MgCl_2$ and 0.1% gelatin) and was used to infect again NM 538 and NM 539 bacteria. The whole procedure was repeated, but in this case on eight of the ten plates greater than 50% of the plaques were red, that is to say contained protein G. New plaques were picked, and the whole procedure was repeated two more times, whereafter red spots which were found on three of the plates corresponded to the total of plaques. As a result, EMBL 3 phage preparations consisting of phages all containing protein G genes were obtained. One of these preparations (named lambda PG4B) was deposited on 29th day of Mar. 1985 at ATCC under number 40176.

5. Production of protein G through infection of *E. coli* bacteria by hybrid DNA molecules consisting of streptococcal DNA and EMBL 3 phage DNA.

The EMBL 3 phages containing protein G genes prepared and purified as described above were used for infecting NM 538 and NM 539 bacteria. A colony of NM 538 and a colony of NM 539 were added respectively to two beakers, each containing 100 ml of LB maltose medium with 10 mM $MgCl_2$. Furthermore, 100 microliters of EMBL 3 phages containing protein G genes were added to each of the two beakers. The beakers were incubated for 8 hours whilst being shaken at 37° C. Bacteria and bacterial residues were centrifuged (10,000 ×G for 20 minutes). The supernatant was analyzed for protein G with the help of peroxidase marked antibodies and with pure protein G as a standard. In the supernatant 5–10 nanograms of protein G/ml were detected. This protein G has been analyzed by the Western blot procedure making use of radioactively marked IgG as a probe, and the molecular weight was determined at approximately 60,000 Daltons.

6. Cloning of protein G genes in lambda gt 11 vector

EMBL 3 DNA containing a 20 kb sized protein G DNA fragment was isolated from lytic plaques. EMBL 3 DNA alone, which does not contain any foreign DNA, cannot be cleaved by the restriction enzyme EcoRI because it lacks an EcoRI site. On the other hand, the 20kb sized fragment could be cleaved by this enzyme. EcoRI cleaved outside the protein G genes making isolation of a smaller DNA fragment containing protein G genes possible.

The EcoRI treated DNA material wa ligated with DNA from lambda phage gt 11. The ligation and subsequent construction of an intact phage particle was done by the same method as described above for EMBL 3. Subsequently, the *E. coli* strain Y1090 (ATCC Rockville, Maryland, USA) was infected with these lambda gt 11 phages, in accordance with the procedure described for EMBL 3. In the analysis of the plates it was found that all plaques contained protein G. From the plates lambda gt 11 phages were purified in a conventional manner. Phage DNA was isolated and the streptococcal DNA which had been ligated with phage DNA was again cut out with EcoRI. Analysis by electrophoresis showed that this DNA fragment containing protein G genes is 4.4 kb in size. Hybrid DNA molecules constructed from lambda gt 11 DNA and this 4.4 kb sized DNA fragment were also used in order to infect another *E. coli* strain (Y1089 ATCC). This strain makes possible an incorporation of the hybrid DNA molecule into the *E. coli* genome when stable lysogens have been achieved.

To sum up, it can be said that it is possible in accordance with the invention, to incorporate protein G genes into bacteriophage DNA and to infect cells with hybrid DNA molecules enabling the synthesis of protein G, fragments of protein G, and/or the IgG binding sites of protein G.

It will be understood that the embodiments described herein are merely exemplary and that a person skilled in the art may make many variations and modifications without departing from the spirit and scope of the invention. All such modificiations and variations are intended to be included within the scope of the invention as defined in the appended claims.

We claim:

1. A recombinant DNA molecule comprising a nucleotide sequence selected from the group consisting of a DNA sequence encoding Protein G or a DNA sequence encoding a biologically active fragment thereof which has the IgG binding specificity of Protein G.

2. A DNA molecule according to claim 1, wherein the DNA sequence comprises about 4.4 Kb.

3. A DNA molecule according to claim 1, wherein the DNA sequence further comprises replication, transcription and translation regulatory sequences; said sequences being operably linked thereto.

4. An EMBL 3 lambda phage comprising the recombinant molecule of claim 1.

5. An EMBL 3 lambda phage of claim 4, wherein the phage is lambda pG4B and has the ATCC Accession Number 40176.

6. A bacterial host cell transformed with the recombinant DNA molecule of claim 1.

7. The transformed host cell of claim 6, being the *E. coli*. bacterium.

8. A method for isolating a bacterial host cell transformed with a DNA molecule encoding Protein G, or a biologically active fragment thereof which has the IgG binding specificity of Protein G, comprising
   identifying a first bacterial host cell known to express Protein G;
   extracting DNA encoding said Protein G from the host cell;
   digesting the DNA with a restriction enzyme to construct a recombinant DNA library;
   transforming a second bacterial host cell, which lacks the ability to express Protein G, with the recombinant DNA library;
   culturing the transformed host cell under conditions effective to allow the expression of the protein or a biologically active fragment thereof; and
   selecting a transformed host cell expressing Protein G, or a biologically active fragment thereof which has the IgG binding specificity of Protein G, by affinity-binding to a labeled IgG antibody.

9. The method of claim 8, wherein the bacterium is a Streptococcus bacterium.

10. The method of claim 8, wherein the DNA sequence which encodes Protein G comprises 4.4 Kb.

11. The method of claim 8, wherein the second bacterial host is *E. coli*.

12. The method of claim 8, wherein the selection of the transformed cell line is conducted with a labeled IgG antibody selected from the group consisting of radiolabeled antibodies and enzyme-labeled antibodies.

13. A recombinant DNA molecule consisting of a DNA segment of about 4.4 Kb in length wherein said DNA molecule encodes an approximately 60,000 molecular weight protein having the IgG binding specificity of Streptococcus G148 Protein G, or a biologically active fragment thereof which has the IgG binding specificity of Protein G.

14. A recombinant DNA molecule of claim 13 operably linked to expression regulatory sequences, said regulatory sequences providing the ability to express the product encoded by the DNA molecule upon transformation and cultivation of a bacterial host cell.

15. The DNA molecule of claim 14, wherein the regulatory sequences comprise regulatory sequences from a Streptococcus bacterium.

16. A method of producing a protein having the IgG binding specificity of Protein G, comprising
   identifying a first bacterial host cell known to express the IgG binding specificity of Protein G;
   extracting DNA encoding said protein from the host cell;
   digesting the DNA with a restriction enzyme to construct a recombinant DNA library;
   transforming a second bacterial host cell, which lacks the ability to express the IgG binding specificity of Protein G, with the recombinant DNA library;
   culturing the transformed host cell under conditions effective to allow the expression of the protein;
   selecting a transformed host cell expressing the protein which has the IgG binding specificity of Protein G, by affinity-binding to a labeled IgG antibody;
   culturing the selected transformed host cell in an expression medium under conditions effective to express the protein; and
   separating the protein from the medium.

17. The method of claim 16, wherein the bacterium is a Steptococcus bacterium.

* * * * *